(12) United States Patent
Sunwoo et al.

(10) Patent No.: US 12,405,528 B2
(45) Date of Patent: Sep. 2, 2025

(54) METHOD OF MANUFACTURING ANTIBACTERIAL COVER WINDOW, AND ANTIBACTERIAL COVER WINDOW MANUFACTURED THEREBY

(71) Applicant: UTI INC., Chungcheongnam-do (KR)

(72) Inventors: Kukhyun Sunwoo, Gyeonggi-do (KR); Tea Joo Ha, Chungcheongnam-do (KR); Jae Suk Oh, Gyeonggi-do (KR); Jung Cheol Noh, Jeollabuk-do (KR)

(73) Assignee: UTI INC., Chungcheongnam-do (KR)

( * ) Notice: Subject to any disclaimer, the term of this patent is extended or adjusted under 35 U.S.C. 154(b) by 631 days.

(21) Appl. No.: 17/493,470

(22) Filed: Oct. 4, 2021

(65) Prior Publication Data
US 2022/0117105 A1    Apr. 14, 2022

(30) Foreign Application Priority Data
Oct. 12, 2020  (KR) .................. 10-2020-0130847

(51) Int. Cl.
| | |
|---|---|
| B08B 17/06 | (2006.01) |
| A61L 2/232 | (2006.01) |
| A61L 2/238 | (2006.01) |
| G03F 7/00 | (2006.01) |
| G03F 7/16 | (2006.01) |
| H05K 5/03 | (2006.01) |
| A61L 101/26 | (2006.01) |

(52) U.S. Cl.
CPC ............ *G03F 7/0002* (2013.01); *A61L 2/232* (2013.01); *A61L 2/238* (2013.01); *G03F 7/162* (2013.01); *H05K 5/03* (2013.01); *A61L 2101/26* (2020.08)

(58) Field of Classification Search
CPC ....................................................... B08B 17/06
USPC ............................................................ 428/98
See application file for complete search history.

(56) References Cited

U.S. PATENT DOCUMENTS

| | | | |
|---|---|---|---|
| 2018/0272048 A1* | 9/2018 | Gifford ................... | A61L 27/50 |
| 2020/0061248 A1* | 2/2020 | Kawaguchi ............... | B32B 9/00 |
| 2022/0063178 A1* | 3/2022 | Raymond ............... | B08B 17/06 |

FOREIGN PATENT DOCUMENTS

| | | | |
|---|---|---|---|
| JP | 2000289149 A | * | 10/2000 |
| JP | 2013-119041 A | | 6/2013 |
| JP | 2016-004623 A | | 1/2016 |
| JP | 2020-513967 A | | 5/2020 |

(Continued)

OTHER PUBLICATIONS

JP2000289149 translation (Year: 2000).*

*Primary Examiner* — Cachet I Proctor
(74) *Attorney, Agent, or Firm* — Mendelsohn Dunleavy, P.C.

(57) ABSTRACT

Disclosed is a method of manufacturing an antibacterial cover window. The method includes a first step of preparing a substrate, a second step of forming a mask pattern on the substrate through a patterning process, a third step of forming an antibacterial layer on the substrate on which the mask pattern is formed, and a fourth step of removing the mask pattern to obtain an antibacterial pattern formed on the substrate. Through the method, it is possible to produce a cover window with antibacterial patterns regularly and uniformly distributed over the entire area thereof. Thus, the cover window has long-lasting excellent antibacterial property over the entire area thereof.

5 Claims, 10 Drawing Sheets

(56) References Cited

FOREIGN PATENT DOCUMENTS

KR 1019990081451 A 11/1999
KR 10-0931748 B1 12/2009

* cited by examiner

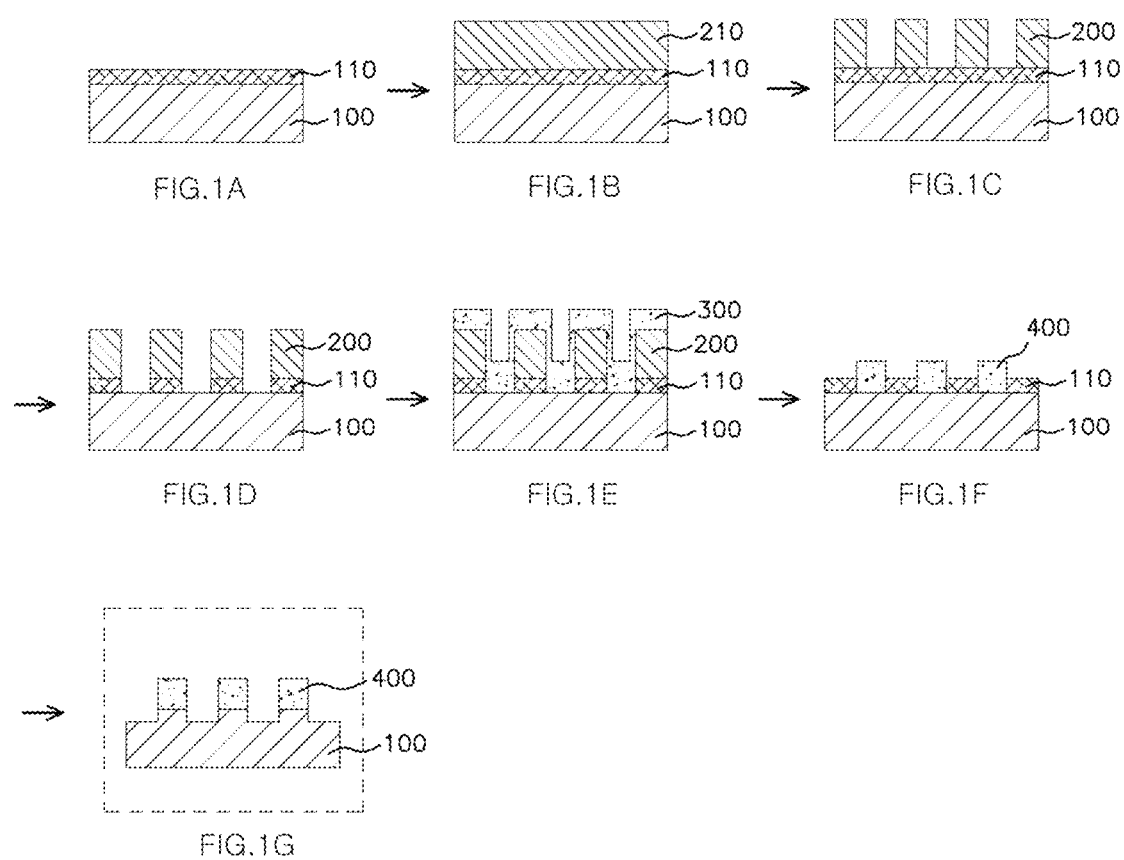

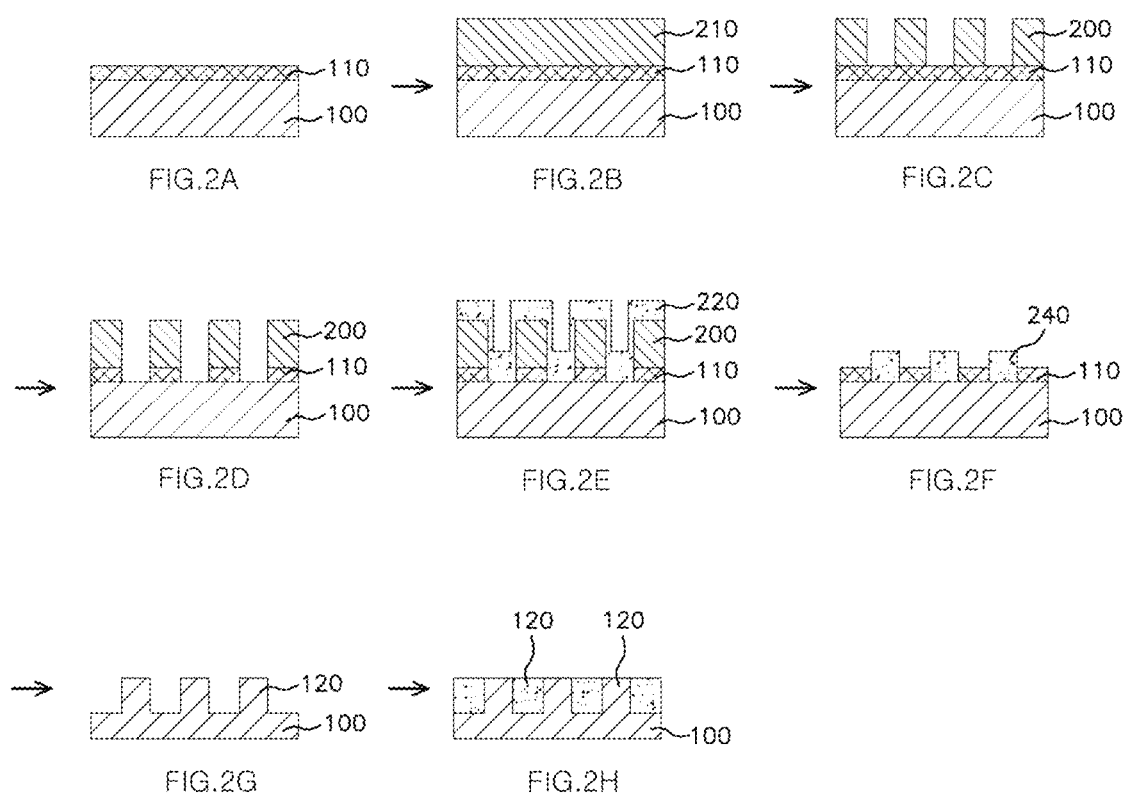

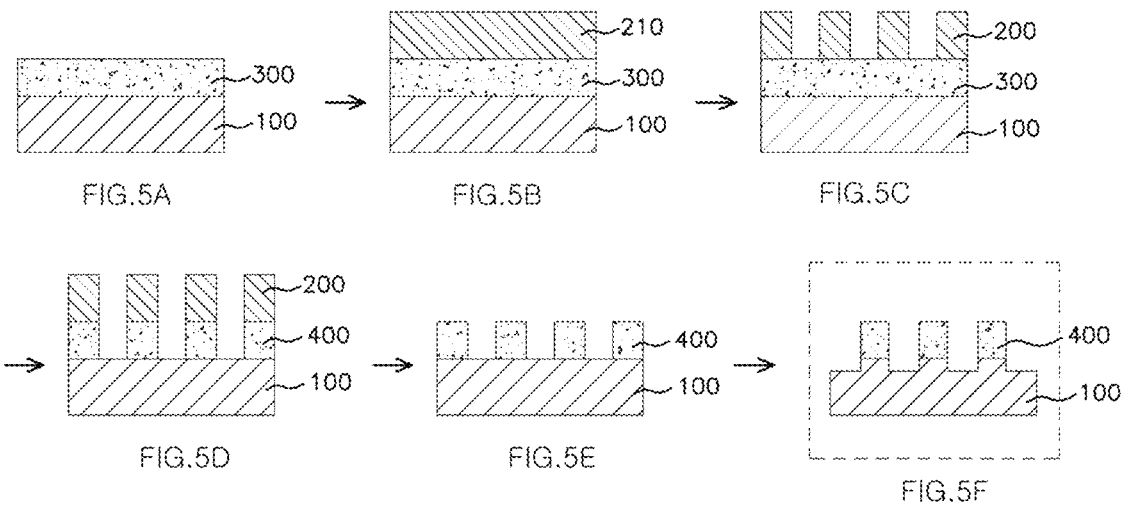
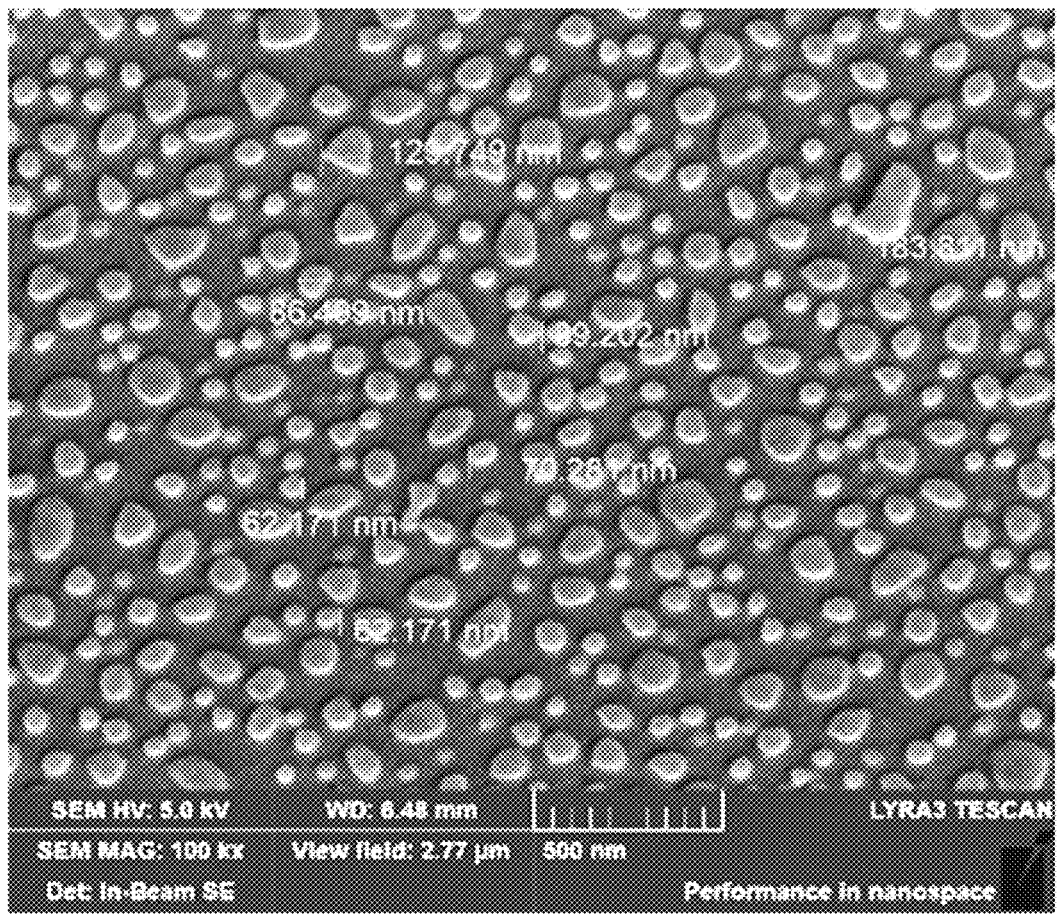
FIG. 6A

METHOD OF MANUFACTURING ANTIBACTERIAL COVER WINDOW, AND ANTIBACTERIAL COVER WINDOW MANUFACTURED THEREBY

CROSS REFERENCE TO RELATED APPLICATION

The present application claims priority to Korean Patent Application No. 10-2020-0130847, filed Oct. 12, 2020, the entire contents of which is incorporated herein for all purposes by this reference.

BACKGROUND OF THE INVENTION

1. Field of the Invention

The present disclosure relates to a cover window. More particularly, the present disclosure relates to a cover window with a long-lasting and excellent antibacterial property over the entire area thereof due to antibacterial patterns that are regularly arranged and uniformly distributed on the surface of a substrate.

2. Description of the Related Art

The gradual development of industry has caused environmental pollution, resulting in the recent global climate change. As a result, at present, diseases caused by new viruses, parasites, and bacteria are increasing. For the reason, research on antibacterial products is being actively conducted around the world.

A simple method of imparting antibacterial properties to a target object includes coating an antibacterial material on the surface of the target object or attaching an antibacterial film to the surface of the target object.

Silver (Ag) and copper (Cu) nanoparticles are the most used antibacterial materials. There are various products coated with silver or copper nanoparticles. However, there is a problem in that the nanoparticles coated on the products easily peel off with time, thereby not being able to perform an antibacterial property after a certain period of time.

Therefore, recently, antibacterial films have been widely used since they are conveniently applied on various products.

Specifically, these antibacterial films are coated on or attached to elevator operation buttons used by many people, touch panels of various electronic devices, and operation buttons of various products.

However, since existing antibacterial films are such that an antibacterial material is simply provided in the form of a coating on the surface of a substrate, there remains a problem in that the antibacterial material peels off over time.

In addition, when such an antibacterial film is coated on the surface of a product, the film also plays a role of protecting the surface of the product to some extent. However, since the antibacterial film itself is gradually damaged over time, the film cannot permanently protect the product, and the antibacterial performance gradually decreases over time.

In addition, since a conventional antibacterial film is formed through a process in which an antibacterial material is simply jetted or spray toward the upper surface of a substrate, there is likelihood that the thickness of the deposited antibacterial material on the substrate is not uniform, resulting in poor uniformity in the antibacterial property throughout the entire area, and it is difficult to control the antibacterial property as desired.

SUMMARY OF THE INVENTION

The objective of the present disclosure is to provide a method of manufacturing an antibacterial cover window having an excellent, uniform, and long-lasting antibacterial property throughout the entire area thereof by adopting a process of forming an antibacterial pattern on a substrate.

A technical ideal of the present disclosure to achieve the above objective is to provide a method of manufacturing an antibacterial cover window, the method including: a first step of preparing a substrate; a second step of forming a mask pattern on the substrate through a patterning process; a third step of forming an antibacterial layer on the substrate on which the mask pattern is formed; and a fourth step of removing the mask pattern to obtain an antibacterial pattern formed on the substrate.

Another technical idea of the present disclosure is to provide a method of manufacturing an antibacterial cover window, the method including: (a) preparing a substrate; (b) forming an antibacterial layer on the substrate; (c) forming a mask pattern on the antibacterial layer through a patterning process; (d) performing an etching process using the mask pattern as an etching mask; and (e) removing the mask pattern to obtain an antibacterial pattern formed on the substrate.

A further technical idea of the present disclosure is to provide an antibacterial cover window including a substrate and an antibacterial pattern formed on the substrate. The antibacterial pattern is an embossed pattern protruding from the upper surface of the substrate or an inlay pattern embedded in a sunken design etched into the surface of the substrate.

The method may further include a step of controlling the surface shape of the antibacterial pattern, and the step may be performed after the fourth step or step (e).

The patterning of the second step or step (c) may be performed by any one method selected from among nano-imprint lithography (NIL), e-beam lithography, polymer blend lithography (PBL), and block copolymer processing (BCP).

The antibacterial pattern may be an embossed antibacterial pattern or an inlay antibacterial pattern.

The antibacterial pattern may be made of one material or a mixture of two or more materials selected from among silver, platinum, copper, and titanium dioxide.

The antibacterial pattern has a pencil hardness in the range from 3H to 9H, an average horizontal width in the range from 50 to 5000 nm, an average interval in the range from 50 to 5000 nm, and an average height in the range from 0.5 to 500 nm.

The method may further include a step of forming a hard mask pattern layer on the substrate on which the mask pattern that is formed in the second step and a step of removing the mask pattern to obtain a hard mask pattern.

Moreover, it is preferable that the substrate is glass or a polymer film.

The present disclosure provides a method of forming a cover window with a long-lasting excellent antibacterial property over the entire area by forming antibacterial patterns that are regularly arranged and uniformly distributed on the surface of a substrate.

In addition, due to the formation of embossed antibacterial patterns and inlay antibacterial patterns, the antibacterial property is improved and the bonding strength between the substrate and the antibacterial material is increased. For these reasons, the cover window exhibits improved abrasion resistance and a long-lasting antibacterial property.

That is, in the present disclosure, the antibacterial pattern is an embossed antibacterial pattern protruding from the surface of the substrate or an inlay antibacterial pattern embedded in an intaglio pattern etched into the substrate. Therefore, cover windows manufactured by the method provided by the present disclosure have a uniform antibacterial property over the entire area thereof and exhibit strong bonding strength between the substrate and the antibacterial pattern, resulting in improvement in the abrasion resistance of the antibacterial pattern. Therefore, the cover windows can be used protective cover windows in various applications.

In addition, since the flexible cover window according to the present disclosure has a pencil hardness of 3H to 9H, the flexible cover window according to the present disclosure is expected to be practically used due to the ability to exhibit an antibacterial property and the ability to protect the surface of a flexible display.

BRIEF DESCRIPTION OF THE DRAWINGS

FIGS. 1A to 1G are schematic diagrams illustrating a method of manufacturing a flexible cover window, according to various embodiments of the present disclosure;

FIGS. 2A to 2H are schematic diagrams illustrating a method of manufacturing a flexible cover window, according to various embodiments of the present disclosure;

FIGS. 5A to 5F are schematic diagrams illustrating a method of manufacturing a flexible cover window, according to various embodiments of the present disclosure;

FIGS. 6A and 6B are scanning electron microscopy (SEM) images illustrating the surfaces of respective cover windows according to embodiments of the present disclosure;

DESCRIPTION OF THE PREFERRED EMBODIMENTS

Figures 3A, 3B, 3C:
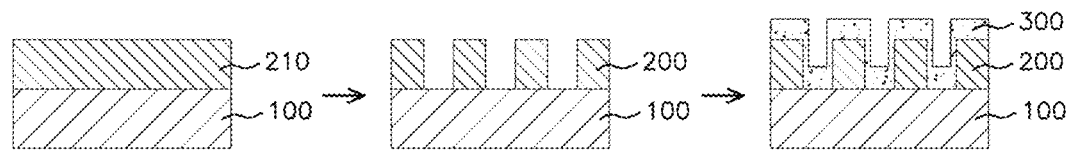
FIGS. 3A to 3E are schematic diagrams illustrating a method of manufacturing a flexible cover window, according to various embodiments of the present disclosure.

The present disclosure relates to a flexible cover window with an antibacterial property. More particularly, the present disclosure discloses a flexible cover window obtained by forming an antibacterial pattern on a substrate so that the flexible cover window has a long-lasting and excellent antibacterial property.

Since the antibacterial pattern used in the present invention is uniformly formed on the surface of a substrate so that the surface of the substrate is imparted with a uniform antibacterial property. In addition, since the antibacterial pattern is formed in an embossed or engraved shape, the flexible cover window disclosed in the present disclosure has sufficient strength as well as an antibacterial property.

That is, in the present disclosure, the antibacterial pattern is an embossed antibacterial pattern protruding from the surface of the substrate or an inlay antibacterial pattern embedded in an intaglio pattern etched into the substrate. Therefore, cover windows manufactured by the method provided by the present disclosure have a uniform antibacterial property over the entire area thereof and exhibit strong bonding strength between the substrate and the antibacterial pattern, resulting in improvement in the abrasion resistance of the antibacterial pattern. Therefore, the cover windows can be used protective cover windows in various applications.

Herein below, exemplary embodiments of the present disclosure will be described in detail with reference to the accompanying drawings. FIGS. 1A to 5F are schematic diagrams illustrating antibacterial cover window manufacturing methods according to various embodiments of the present disclosure, and FIGS. 6A to 10B are SEM images illustrating the surfaces of the cover windows manufactured by the methods according to various embodiments of the present disclosure.

As illustrated in the drawings, an antibacterial cover manufacturing method according to one embodiment of the present disclosure includes a first step of preparing a substrate 100, a second step of forming a mask pattern 200 on the substrate 100 using a patterning process, a third step of forming an antibacterial layer 300 on the substrate 100 on which the mask pattern 200 is formed, and a fourth step of removing the mask pattern 200 to an antibacterial pattern 400 on the substrate 100.

The present invention features the formation of the mask pattern 200 on the substrate 100 by a patterning process and the formation of the antibacterial pattern 400 on the substrate 100.

The antibacterial pattern 400 thus formed is an embossed antibacterial pattern 400 protruding from the surface of the substrate 100 or an inlay antibacterial pattern 400 embedded in the substrate 100. The inlay antibacterial pattern 400 is formed by etching a surface layer of the substrate 100 to form an intaglio pattern recessed from the surface of the substrate 100 and filling the intaglio pattern with an antibacterial material. Therefore, a uniform antibacterial property and strong bonding strength between the substrate 100 and the antibacterial pattern 400 can be obtained, resulting in improvement in the abrasion resistance and long-lasting retention of the antibacterial property of the antibacterial pattern 400. Therefore, the cover windows manufactured by the method disclosed herein can be used as protective cover windows in various products.

FIGS. 1A to 1G and FIGS. 3A to 3E relate to a method of forming an embossed antibacterial pattern 400 on a substrate 100 according to an embodiment of the present disclosure, and FIGS. 2A to 2H and 3A to 3E relate to a method of forming an inlay antibacterial pattern 400 on a substrate 100 according to another embodiment of the present disclosure.

Accordingly, an antibacterial cover window according to the present disclosure includes a substrate 100 and an antibacterial pattern 400 formed on the substrate 100. The antibacterial pattern 400 may be an embossed antibacterial pattern protruding from the surface of the substrate 100 or an inlay antibacterial pattern 400 embedded in an intaglio pattern 120 etched into the surface of the substrate 100.

First, in one embodiment of the present disclosure, as the substrate 100, a glass film or polymer film is prepared (first step).

In the case of using a glass plate as the substrate 100, a thin glass plate having a thickness of 30 to 300 μm is attached to the surface of a target object such as an operation panel, an operation button, or a touch panel so as to serve as a protective window cover.

Alternatively, the substrate 100 may use a polymer film such as PVC, synthetic resin, plastic, acrylic, vinyl, or any polymer. The material of the substrate 100 may be selected depending on the purpose and specifications of a target product, and the substrate 100 may be used as a window cover.

Next, a mask pattern 200 is formed on the substrate 100 by a patterning process (second step).

The patterning may be performed by any one method selected from among nano-imprint lithography (NIL), e-beam lithography, polymer blend lithography (PBL), and block copolymer processing (BCP).

In an embodiment of the present disclosure, block copolymer processing (BCP) or polymer blend lithography (PBL) among the patterning processes will be described.

FIGS. 1A to 1G and FIGS. 2A to 2H are schematic views illustrating antibacterial cover window manufacturing methods in which the BCP is used as the patterning process. FIGS. 3A to 3E and FIGS. 4A to 4G are schematic diagrams illustrating antibacterial cover window manufacturing methods in which the PBL is used as the patterning process. FIGS. 5A to 5G are schematic diagrams illustrating an antibacterial cover window manufacturing method in which the PBL is used as the patterning process, according to another embodiment of the present disclosure.

The BCP and PBL are patterning methods using a heterogeneous polymer structure. Specifically, a polymer layer 210 including different polymers is formed on the substrate 100, phase separation between the different polymers included in the polymer layer 210 is induced, and any one of the polymers separated through the phase separation is removed from the substrate 100 while the other polymer remains on the substrate 100 so as to serve as the mask pattern 200.

The heterogeneous polymer structure is formed by bonding or mixing two or more polymers having different properties. As the polymers to form the heterogeneous polymer structure, any polymers can be used without limitation if they can be separated through the phase separation.

In one embodiment of the present disclosure, as the heterogeneous polymer structure, a block copolymer including a polymer A block and a polymer B block having different properties or a polymer mixture including a first polymer A and a second polymer B is used. Such a block copolymer or a polymer mixture may be available in the form of a solution when a solvent is added thereto. The solvent may be a solvent exhibiting a different solubility or a solvent exhibiting the same solubility for each of the polymers used.

First, in the block copolymer, two or more chemically different blocks are covalently bonded, and the phase separation structure and size thereof vary depending on the chemical properties, length (or molecular weight), composition ratio, and annealing temperature of each block.

On the other hand, the polymer mixture is formed by mixing two or more chemically different polymers to form a heterogeneous mixture, and the phase separation structure and size vary depending on the chemical properties, molecular weight, mixing ratio, annealing temperature, etc. of each polymer.

In particular, the first polymer A and the first polymer B constituting the block copolymer or the polymer mixture have different properties. That is, they are incompatible. For example, the first polymer A and the second polymer B may have different solubilities due to the difference in their respective chemical structure. Since one phase made of any one polymer has higher solubility than the other phase phase made of a different polymer, any one polymer can be selectively and easily removed than the other.

Specifically, for the block copolymer, a polymer A block derived from styrene or a derivative thereof and a polymer B block derived from an acrylic acid ester may be combined.

For example, the block copolymer is preferably a block copolymer selected from among a polystyrene (PS)-polymethyl methacrylate (PMMA) block copolymer, a polystyrene (PS)-polybutadiene (PB) block copolymer, and a polystyrene (PS)-polydimethylsiloxane (PDMS) block copolymer.

In addition, specifically, the polymer mixture may be a heterogeneous mixture including a polymer A derived from styrene or a derivative thereof and a polymer B derived from an acrylic acid ester.

For example, the block mixture is preferably a polymer mixture selected from among a polystyrene (PS)-polymethyl methacrylate (PMMA) polymer mixture, a polystyrene (PS)-polybutadiene (PB) polymer mixture, and a polystyrene (PS)-polydimethylsiloxane (PDMS) polymer mixture.

The polymer layer 210 may be formed on the substrate 100 by a known method, such as spin coating. Referring to FIGS. 1A to 1G and 2A to 2H, before the polymer layer 210 is formed, a neutral layer 110 on the substrate 100 is first processed.

The neutral layer 110 is used to effectively induce the phase separation of the vertical structures on the substrate 100. Thus, the neutral layer 110 exhibits a neutral affinity to two different polymers constituting the heterogeneous polymer structure. That is, the neutral layer 110 does not exhibit a higher affinity to any one of the two polymers.

That is, since the polymers on the surface of the neutral layer 110 exhibit an equal affinity, it is effective to form phase-separated structures forming a vertical structure.

The neutral layer 110 is formed of an organic material or an inorganic material. In the case of using an inorganic material, hydrophobic treatment using ion implantation may be performed on the surface of an inorganic material layer so that individual polymer blocks may be induced to be vertically oriented.

Next, phase separation between the polymers in each heterogeneous polymer structure included in the polymer layer 210 is induced.

The polymer block components in the block copolymer may reordered by annealing or by spontaneous reordering. That is, a first region A in which the polymer A blocks are ordered and a second region B in which the polymer B blocks are ordered may be formed though phase separation caused by annealing. The shape of each region depends on the chemical properties and length (or molecular weight) of each block, the composition ratio, annealing temperature, etc.

The annealing temperature is typically higher than the glass transition temperature of the block copolymer and is lower than the thermal decomposition temperature. For example, the annealing may be performed at a temperature in the range from 100° C. to 190° C. for a period of time in the range from several tens of seconds to 24 hours.

The first region A composed of the polymer A blocks and the second region B composed of the polymer B blocks form various phase-separated structures depending on the chemical properties of each block, the block length, the composition ratio, the annealing temperature, etc. With proper settings of the parameters, either the first region A or the second region B may serve as a matrix, and the other region may form the mask pattern 200. The region serving as the matrix is selectively removed in a subsequent process.

In addition, the same description applies to the case where a first phase region A and a second phase region B result from the phase separation between a polymer A and a polymer B constituting a polymer mixture.

Here, when the block copolymer is used, the first phase regions and the second phase regions are relatively regularly arranged whereas when the polymer mixture is used, the first phase regions and the second phase regions are relatively irregular depending on the settings of the parameters.

This is because a block copolymer has a heterogeneous structure in which incompatible polymer blocks are covalently linked. The polymer blocks form their respective regions, resulting in regular arrangement of the different phase regions through the phase separation. On the other hand, since a polymer mixture is a mixture in which incompatible polymers are heterogeneously mixed, the pattern composed of the phase-separated polymer regions is relatively irregular.

Of the polymer blocks or polymers that are heterogeneous, the polymer block or polymer in a phase region to be removed to form the antibacterial pattern 400 in the subsequent process has relatively high solubility than the polymer block or polymer in a phase region not to be removed. The remaining polymer block or polymer serve as an etching mask for the subsequent patterning.

Then, any one of the polymer structures in the phase-separated polymer layer 210 is selectively removed to form a mask pattern 200 made of the remaining polymer structure on the substrate 100.

Any one of the polymer structures in the phase-separated polymer layer 210 (i.e., either the first phase region A or the second phase region B) is removed. The polymer structures to be removed and to be retained are designed by controlling the types and molecular weights of polymers, the mixing ratio or composition ratio of the polymers, the annealing temperature, and the like, depending on the finished shape of the antibacterial pattern 400.

According to one embodiment of the present disclosure, the phase separation is first induced using a polystyrene (PS)-polymethylmethacrylate (PMMA) block copolymer, and then the PS or PMMA is selectively removed.

For example, when the PMMA is set as the matrix region, the phase region composed of the PMMA is removed through wet etching, thermal decomposition, UV treatment, or the like which uses the solubility difference between the PS and the PMMA. Here, when thermal decomposition or UV treatment is performed, the PMM with a relatively low molecular weight is removed by a developing process or the like.

By selectively removing one of the phase regions formed by the phase separation of the polymer layer 210 as described above, the mask pattern 200 made of the remaining polymer structure is formed on the substrate 100.

In a third step, the antibacterial layer 300 is formed on the substrate 100 on which the mask pattern 200 is formed. In a fourth step, the mask pattern 200 is removed from the substrate 100 so that the antibacterial pattern 400 is formed on the substrate 100.

The antibacterial layer 300 is formed through a physical or chemical thin film deposition method. According to one embodiment of the present disclosure, the antibacterial layer 300 is formed through a sputtering deposition process. That is, the antibacterial pattern 400 is obtained by forming the antibacterial layer 300 through a deposition process and removing the mask pattern 200 through a lift-off process.

In one embodiment in which the antibacterial pattern 400 is an embossed antibacterial pattern 400, the mask pattern 200 is made of one polymer structure of two different polymer structures and is formed on the substrate 100. The embossed antibacterial pattern 400 is formed by removing the mask pattern 200 from the substrate 100 after forming the antibacterial layer 300 on the substrate on which the mask pattern 200 is formed.

In one embodiment in which the antibacterial pattern 400 is an inlay antibacterial pattern 400, etching is performed on the substrate 100 using the mask pattern 200 as an etching mask to form an intaglio pattern 120 etched into the substrate 100. Next, the antibacterial layer 300 is formed on the substrate 100 having the mask pattern 200 and the intaglio pattern 120 thereon. Next, the mask pattern 200 is removed.

That is, the substrate 100 is etched using the mask pattern 200 made of one polymer structure of two different polymer structures as an etching mask so that the intaglio pattern 120 (i.e., sunken pattern) can be formed on the substrate 100, and the antibacterial layer 300 is then formed on the substrate 100. After that, the mask pattern 200 is removed.

In this case, the mask pattern 200 may be replaced with a hard mask pattern 240 having a higher etch selectivity with respect to the substrate 100 than the mask pattern 200 made of a polymer structure.

For example, as illustrated in FIGS. 2A to 2H and 4A to 4G, after the mask pattern 200 made of a polymer structure is formed, a hard mask pattern layer 220 is formed on the substrate 100, and the polymer structure of the mask pattern 200 is lifted off. Thus, the relatively soft mask pattern 200 made of a polymer structure is removed, and the mask pattern 240 that is harder than the mask pattern 200 is formed.

Here, the hard mask pattern 240 is used as an etching mask for selectively etching the substrate 100. Therefore, the hard mask pattern 240 is made of a material having a high etch selectivity with respect to the substrate 100.

For the simplification of the manufacture, the same process as the process for forming the antibacterial layer 300 to be described later is used, and the same material as the antibacterial layer 300 is used. According to one embodiment of the present disclosure, a sputtering deposition process is used, and a copper or chrome target is used for the sputtering deposition.

After forming the mask pattern 200 on the substrate 100 in the way described above, the antibacterial layer 300 is formed thereon, and the mask pattern 200 is immediately removed to form an embossed antibacterial pattern 400 protruding from the surface of the substrate 100. Alternatively, the surface of the substrate 100 is selectively etched using the mask pattern 200 as an etching mask to form an intaglio pattern 120 recessed from the surface of the substrate 100, and the intaglio pattern 120 is filled with an antibacterial material to form an inlay antibacterial pattern 400. In this case, the intaglio antibacterial pattern 400 may be formed after the hard mask pattern 240 is formed as necessary.

In the present disclosure, the antibacterial pattern 400 is formed on the substrate 100 by depositing an antibacterial material on the substrate 100 exposed through the openings of the mask pattern 200 (or hard mask pattern 240). The antibacterial material may be a metallic material or a non-metallic material exhibiting an antibacterial property.

According to one embodiment of the present disclosure, the antibacterial pattern 400 is formed using any one material or a combination of two or more materials selected from among silver, platinum, copper, and titanium dioxide.

The antibacterial materials exhibit excellent antibacterial activity. Particularly, copper is known to be excellent in removing bacteria. Any one material selected from the above-described materials may be used solely. Alternatively, a mixture of two or more materials may be used. Specifically, a mixture of copper and either one of platinum and titanium dioxide may be used.

The antibacterial pattern 400 is formed by first forming the antibacterial layer 300 on the substrate 100 on which the mask pattern 200 is formed, and then removing the mask pattern 200. The antibacterial layer 300 may be formed by a typical deposition or coating process.

For example, the antibacterial layer 300 may be formed by a sputtering process that is one of conventional thin film formation methods. In this case, a silver, platinum, copper, or titanium dioxide target is used to form the antibacterial layer 300 on the substrate 100 on which the mask pattern 200 is formed.

In addition, the antibacterial layer 300 is formed by a known coating process such as spray coating, dip coating, bar coating, stamping, slot coating, or the like. In this case, an antibacterial resin composition including at least one of silver, platinum, copper, and titanium dioxide is used to form the antibacterial layer 300 on the substrate 100 on which the mask pattern 200 is formed.

The antibacterial resin composition may be a resin composite composition in which at least one kind of nanoparticles among silver, platinum, copper, and titanium dioxide nanoparticles are dispersed in an amount of 0.001 to 0.5 parts by weight. Specifically, a transparent resin such as optical clear resin (OCR) is used. More specifically, any one selected from among acrylic compounds, epoxy, silicone, urethane, urethane compounds, urethane acrylic compounds, hybrid sol-gel, and siloxane-based resin is used. These materials may be mixed in various combinations to control strength and elasticity.

The transparency of the antibacterial pattern 400 can be adjusted by controlling the thickness of the antibacterial layer 300 or the composition ratio of the antibacterial material.

A conventional antibacterial film is formed by coating a substrate with an antibacterial material such as copper particles. In this case, the bonding strength between the substrate and the antibacterial material is not maintained, and the antibacterial material is not uniformly coated on the substrate. Therefore, the antibacterial coating on the substrate 100 is not uniform, resulting in poor uniformity in antibacterial activity on the substrate.

In addition, when used as a cover window for a target object, there is a problem in that the antibacterial material falls off due to frequent contact or friction.

The cover window according to one embodiment of the present disclosure is constructed such that an antibacterial material is formed in a predetermined regular pattern shape on the substrate 100 through a patterning process or is formed in a uniformly dispersed pattern shape. Therefore, the cover window exhibits uniform transparency through the entire area thereof. In addition, since the antibacterial material and the substrate 100 are strongly bound to each other, a problem in which the antibacterial material falls off the substrate 100 does not occur. For the reasons, the cover window retains long-lasting, excellent, and uniform antibacterial activity over the entire area thereof.

The cover window including the antibacterial pattern 400, according to the present disclosure, has a pencil hardness in the range from 3H to 9H.

In general, a coating layer made of a resin is known to have a pencil hardness in the range from 1H to 2H. However, when the antibacterial pattern 400 made of the antibacterial material is formed through deposition or coating so as to be regularly arranged on the substrate 100, the cover window has a pencil hardness in the range from 3H to 9H. Therefore, the cover window of the present disclosure can function to protect the surface of a target object due to the increased hardness as well as exhibits antibacterial activity.

In particular, according to one embodiment of the present disclosure, the antibacterial pattern 400 is formed as an embossed antibacterial pattern or an inlay antibacterial pattern by applying, on the substrate, an antibacterial coating composition composed of a resin coating solution and antibacterial particles dispersed in the resin coating solution. Therefore, even when the substrate 100 is folded or bent, the antibacterial pattern 400 may not be cracked or separated from the substrate 100. Therefore, the cover window disclosed in the present disclosure can be usefully applied to recent wearable electronic products and flexible displays.

Since the cover window exhibits an excellent antibacterial activity, high strength, and good folding characteristics, it can be used as a cover window for a display panel or as a cover window for various operation buttons of electronic products. The cover window also can be used as a cover window for products requiring antibacterial activity or products with a curved surface.

In addition, the antibacterial pattern 400 may be optionally provided with an anti-fingerprint (AF) function or an anti-reflective (AR) function as needed. This function may be realized by using a resin having such a function.

According to another embodiment of the present disclosure, there is provided a method of manufacturing a cover window, the method including (a) preparing a substrate 100, (b) forming an antibacterial layer 300 on the substrate 100, (c) forming a mask pattern 200 on the antibacterial layer 300, using a patterning process, (d) etching the substrate 100 using the mask pattern 200 as an etching mask, and (e) removing the mask pattern 200 to form an antibacterial pattern 400 on the substrate 100.

In this embodiment, the antibacterial layer 300 is formed before the mask pattern 200 is formed. After the mask pattern 200 is formed on the antibacterial layer 300 through a patterning process, the substrate 100 is selectively etched using the mask pattern 200 as an etching mask. Next, the mask pattern 200 is removed so that the antibacterial pattern 400 remains on the substrate 100.

The method may further include a step of controlling the surface shape of the antibacterial pattern 400, and this additional step may be performed after the fourth step of the former embodiment or step (e) of the latter embodiment.

The surface shape control process can be particularly usefully applied to an embodiment in which an embossed antibacterial pattern 400 is formed. This surface shape control process refers to a process of roughening the surface of the antibacterial pattern 400 to have irregularities.

The surface shape control process may be implemented by a dry or wet etching process. The fine irregularities on the surface of the antibacterial pattern 400 further improves antibacterial activity and prevents bacteria from being transferred to the user when the user makes touch on the surface of the cover window.

Hereinafter, various embodiments of the present invention described above will be summarized and described again with reference to the drawings.

FIGS. 1A to 1G and FIGS. 2A to 2H are schematic views illustrating antibacterial cover window manufacturing methods in which the BCP is used as the patterning process, according to embodiments of the present disclosure. FIGS. 3A to 3E and FIGS. 4A to 4G are schematic diagrams illustrating antibacterial cover window manufacturing methods in which the PBL is used as the patterning process, according to embodiments of the present disclosure. FIGS. 5A to 5G are schematic diagrams illustrating an antibacterial cover window manufacturing method in which the PBL is used as the patterning process, according to one embodiment of the present disclosure.

Referring to FIGS. 1A to 1G, a neutral layer 110 is formed on a substrate 100 in step (a). Next, a polymer layer 210 including a block copolymer is formed on the neutral layer 110 in step (b). Next, the phase separation of heterogeneous polymer structures included in the polymer layer 210 is induced, and any one of the polymer structures resulting from the phase separation is removed in step (c). Next, the exposed portions of the neutral layer 110 on the substrate 100 are removed using an RIE ($O_2$ plasma) process to form a mask pattern 200 in step (d). Next, an antibacterial layer 300 is formed on the substrate 100 on which the mask pattern 200 is formed, using a sputtering process in step (e). Next, the mask pattern 200 is removed through a lift-off process in step (f) to form an embossed antibacterial pattern 400 on the substrate 100.

Optionally, a surface shape control process, such as a dry etching process, is performed to remove the neutral layer 110 exposed on the substrate 100, and fine irregularities are formed on the surface of the antibacterial pattern 400 in step (g).

Figure 6B:
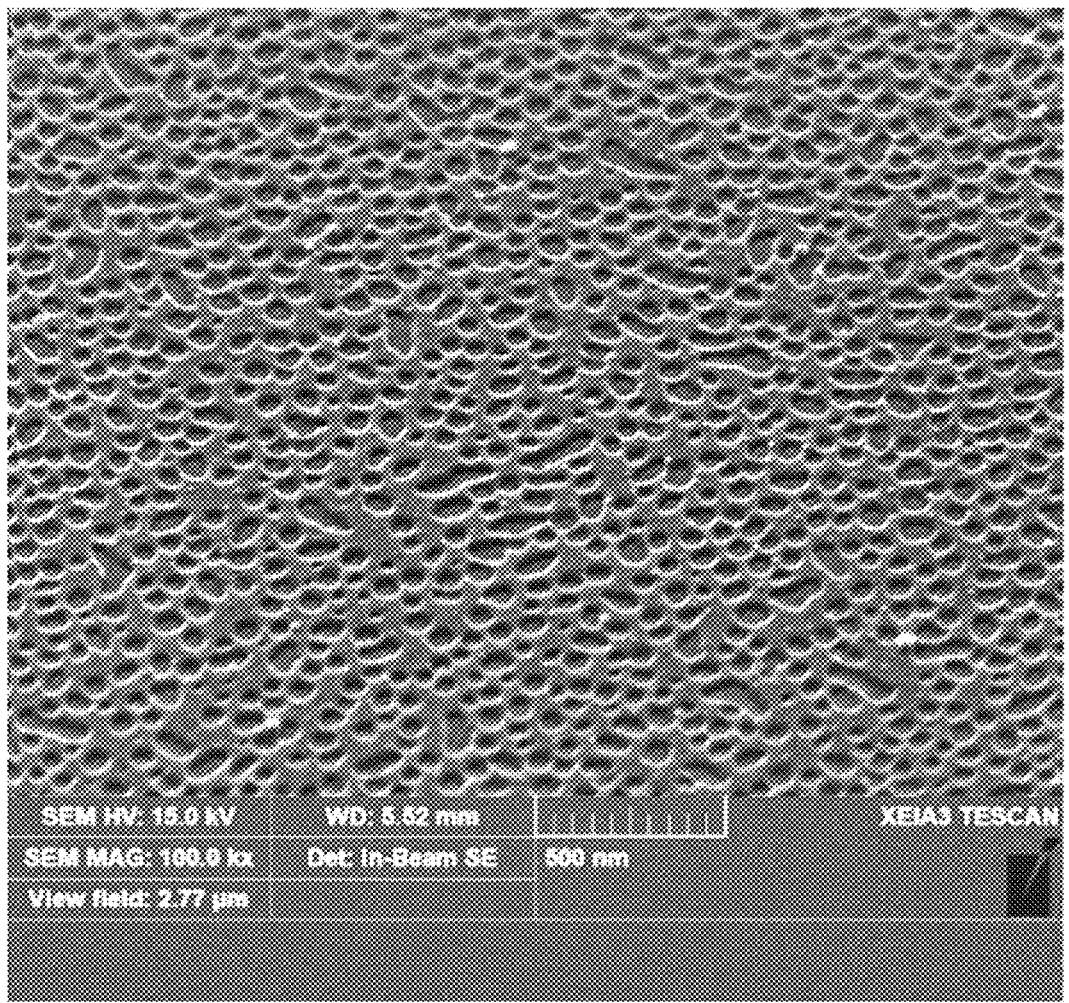

FIGS. 6A and 6B are SEM images showing the surfaces of respective samples after a process corresponding to FIG. 1D is performed. FIG. 6A is an SEM image of the surface of a PMMA pattern according to one embodiment of the present disclosure, and FIG. 6B is an SEM image of the surface of a PS matrix according to one embodiment of the present disclosure.

Figure 7:
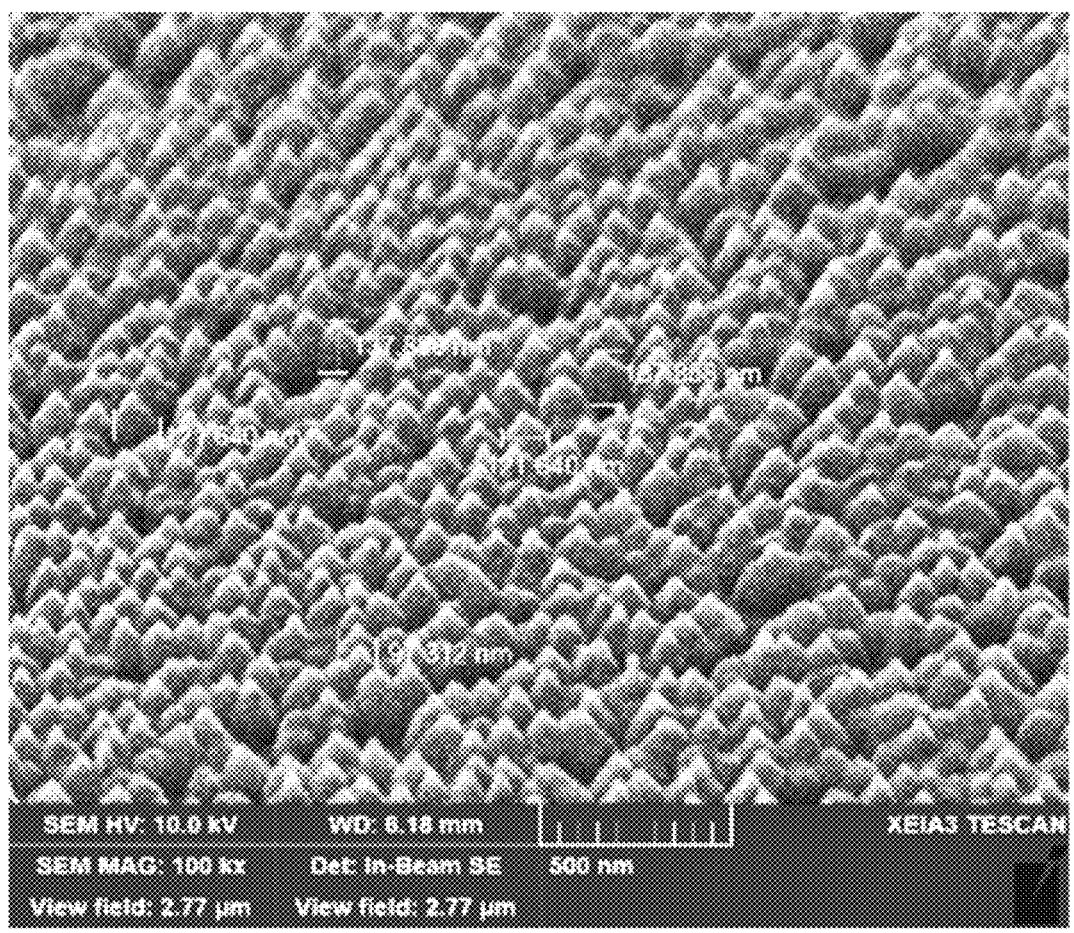
FIG. 7 is an SEM image illustrating the surface of a cover window according to one embodiment of the present disclosure.

FIG. 7 is an SEM image showing the surface of the antibacterial pattern resulting from a process corresponding to FIG. 1E.

Referring to FIGS. 2A to 2H, a neutral layer 110 is formed on a substrate 100 in step (a). Next, a polymer layer 210 including a block copolymer is formed on the neutral layer 110 in step (b). Next, the phase separation of heterogeneous polymer structures included in the polymer layer 210 is induced, and any one of the polymer structures resulting from the phase separation is removed in step (c). Next, the exposed portions of the neutral layer 110 on the substrate 100 are removed using an RIE ($O_2$ plasma) process to form a mask pattern 200 in step (d). Next, a hard mask layer 220 is formed on the substrate 100 on which the mask pattern 200 is formed using a sputtering process, in step (e). Next, the mask pattern 220 made of the polymer structure is lifted off to form a hard mask pattern 240 on the substrate 100 in step (f). Next, a dry etching process is performed using the hard mask pattern 240 as an etching mask to form an intaglio pattern 120 on the substrate 100 in step (g). The intaglio pattern 120 is filled with an antibacterial material to form an inlay antibacterial pattern 400 in step (h).

Referring to FIGS. 3A to 3E, a polymer layer 210 including a polymer mixture is formed on a substrate 100 in step (a). Next, the phase separation of heterogeneous polymer structures included in the polymer layer 210 is induced, and any one of the polymer structures resulting from the phase separation is removed to form a mask pattern 200 in step (b). Next, an antibacterial layer 300 is formed on the substrate 100 on which the mask pattern 200 is formed using a sputtering process, in step (c). Next, the mask pattern 200 is lifted off to form an embossed antibacterial pattern 400 on the substrate 100 in step (d).

A surface shape control process, such as a dry etching process, is performed so that the exposed neutral layer 110 on the substrate 100 is removed and fine irregularities are formed on the surface of the antibacterial pattern 400 in step (e).

Figures 3D, 3E:
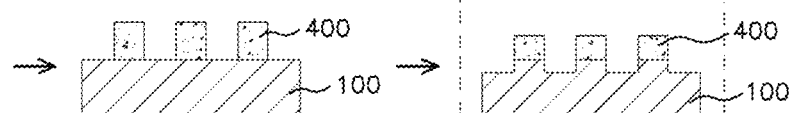
Figures 4A, 4B, 4C:
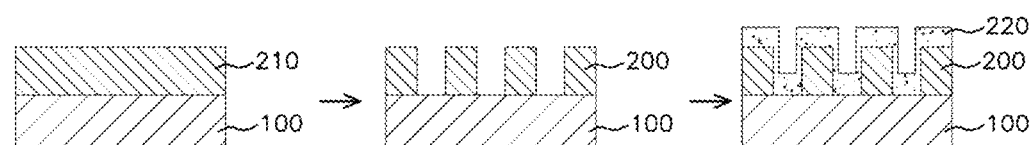
FIGS. 4A to 4G are schematic diagrams illustrating a method of manufacturing a flexible cover window, according to various embodiments of the present disclosure.
Figures 4D, 4E, 4F:
Figure 4G:
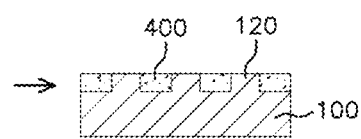
Figure 8:
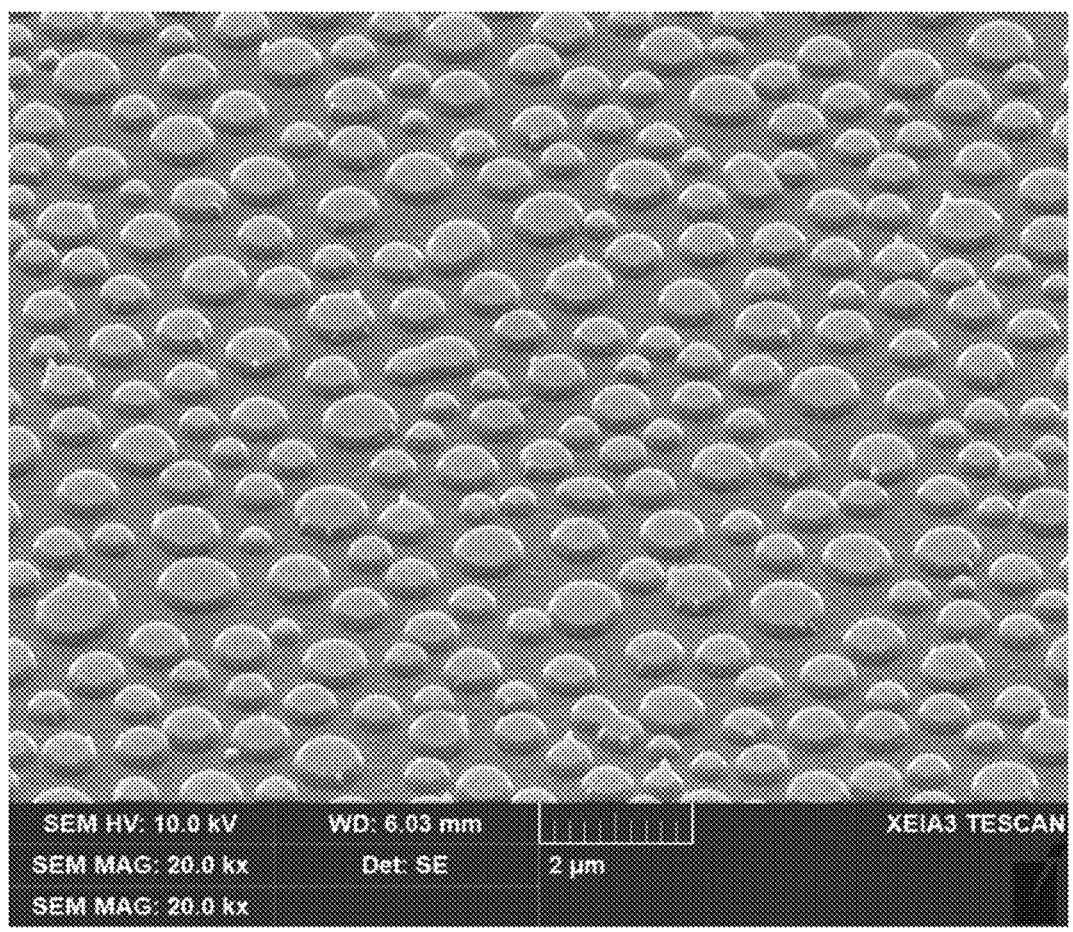
FIG. 8 is an SEM image illustrating the surface of a cover window according to one embodiment of the present disclosure.
Figure 9:
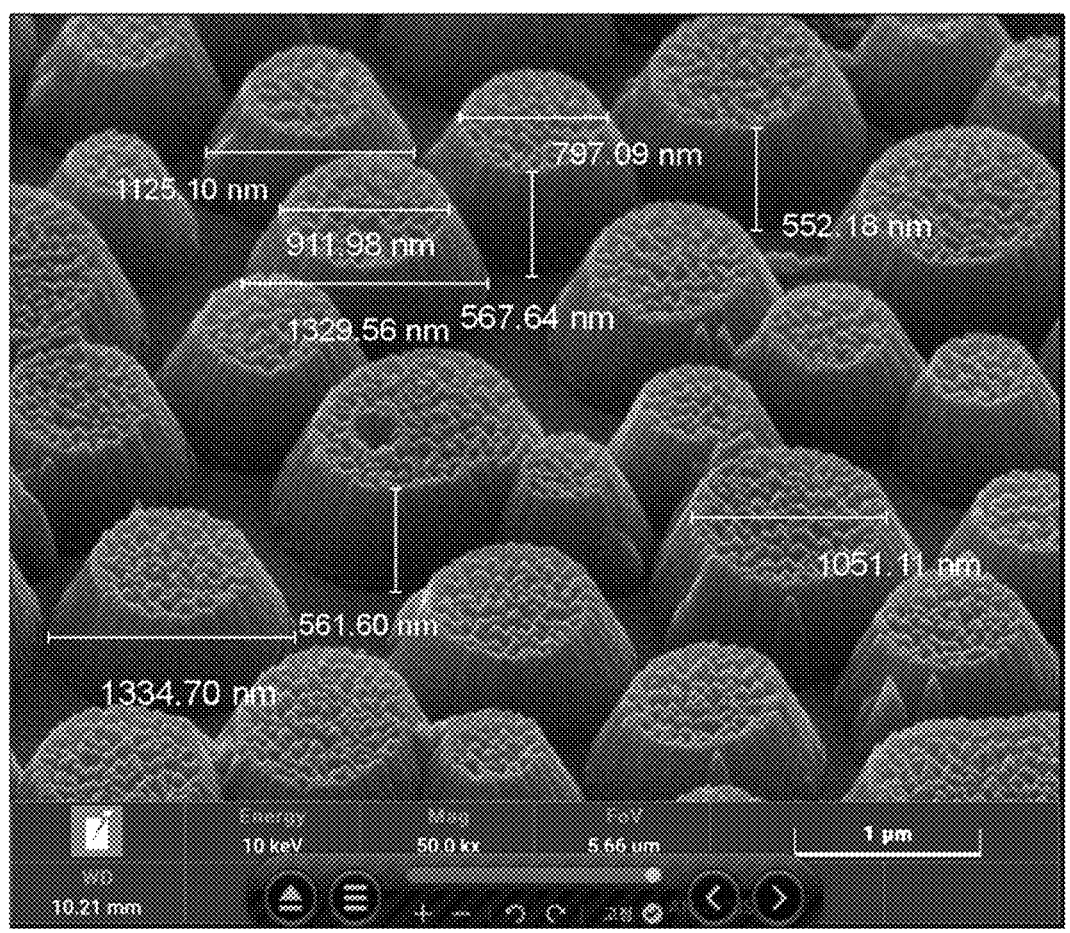
FIG. 9 is an SEM image illustrating the surface of a cover window according to one embodiment of the present disclosure.

FIG. 8 is an SEM image showing the surface of a sample resulting from the process corresponding to FIG. 3D. The SEM image shows that the surface of the antibacterial pattern is even. FIG. 9 is an SEM image showing the surface of a sample resulting from the process corresponding to FIG. 3E. The SEM image shows that the surface of the antibacterial pattern is not even.

Referring to FIGS. 4A to 4G, a polymer layer 210 including a polymer mixture is formed on a substrate 100 in step (a). Next, the phase separation of polymer structures included in the polymer layer 210 is induced, and any one of the polymer structures resulting from the phase separation is removed to form a mask pattern 200, in step (b). Next, a hard mask layer 220 is formed on the substrate 100 on which the mask pattern 200 is formed, using a sputtering process in step (c). Next, the mask pattern 220 made of the polymer structure is lifted off to form a hard mask pattern 240 on the substrate 100 in step (d). Next, a dry etching process is performed using the hard mask pattern 240 as an etching mask to form an intaglio pattern 120 on the substrate 100 in step (e) and step (f). Next, the intaglio pattern 120 is filled with an antibacterial material to form an inlay antibacterial pattern 400 in step (g).

Referring to FIGS. 5A to 5F, an antibacterial layer 300 is formed on a substrate 100 in step (a). Next, a polymer layer 210 including a polymer mixture is formed on the antibacterial layer 300 in step (b). Next, the phase separation of polymer structures included in the polymer layer 210 is induced, and any one of the polymer structures resulting from the phase separation is removed to form a mask pattern 200 in step (c). Next, an etching process is performed using the mask pattern 200 as an etching mask in step (d), and the mask pattern 200 is then removed using a stripping process in step (e). Thus, an embossed antibacterial pattern 400 remains on the substrate 100 in step (f).

Figure 10A:
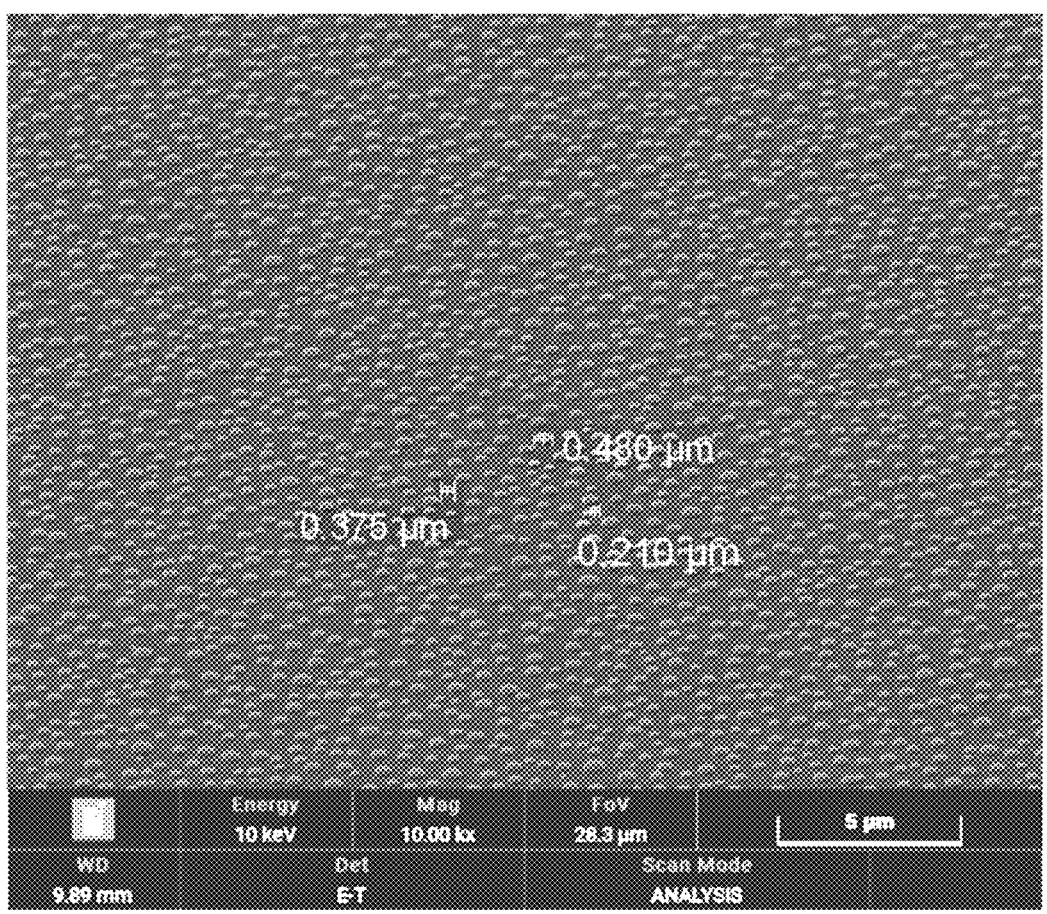
FIGS. 10A and 10B are SEM images illustrating the surfaces of respective cover windows according to embodiments of the present disclosure.
Figure 10B:
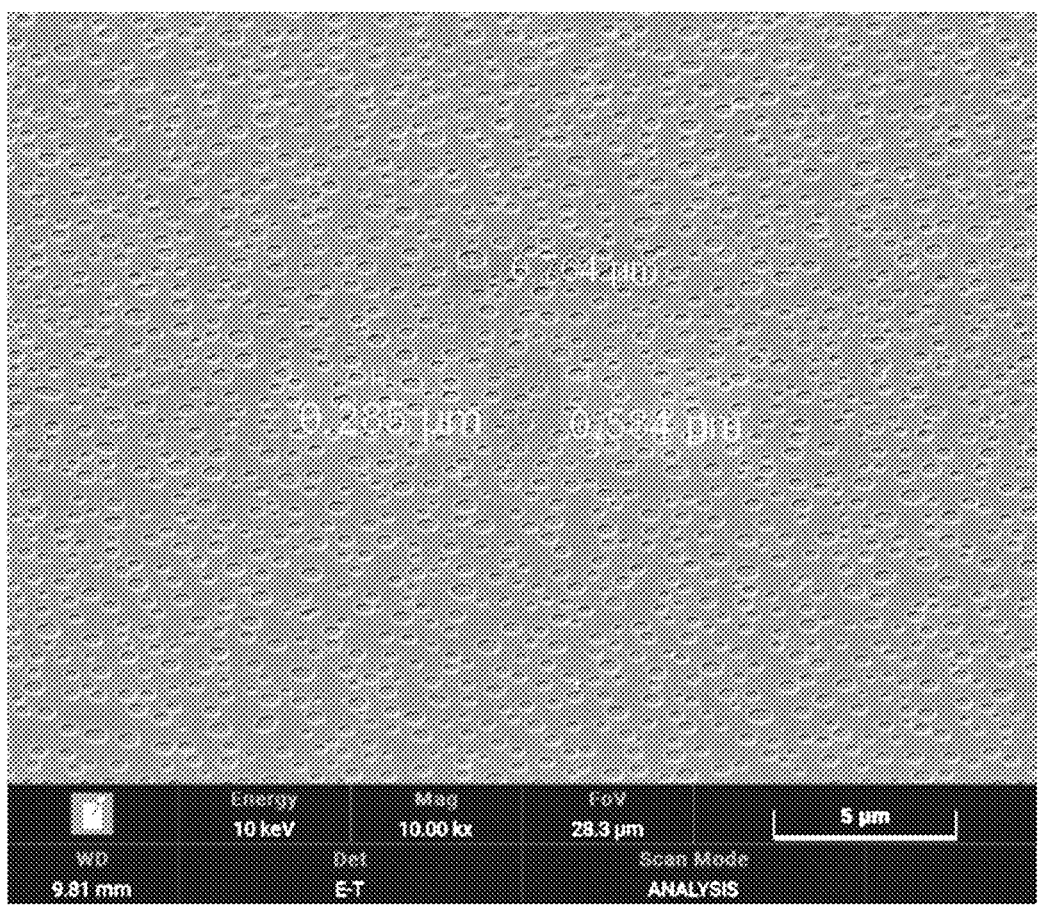

FIGS. 10A and 10B are SEM images showing the surface of a sample resulting from the process corresponding to FIG. 5C. FIG. 10A is an SEM image showing the surface of a PS pattern according to one embodiment of the present disclosure, and FIG. 10B is an SEM image showing the surface of a PMMA matrix according to one embodiment of the present disclosure.

In one example of the present disclosure, a sputtering process was performed on a glass substrate having a thickness of about 150 μm. In the sputtering process, a copper target was used to form spherical embossed antibacterial patterns on the glass substrate. The patterns had an average diameter of 50 nm and an average height of 50 nm and are spaced from each other at intervals of 50 nm.

Table 1 shows data of an antibacterial activity test for Example of the present disclosure and Comparative Examples.

TABLE 1

| Classification | Antibacterial activity | | Staphylococcus aureus | | Coli | | Bacteria reduction (%) | |
|---|---|---|---|---|---|---|---|---|
| | Staphylococcus aureus | Coli | Control | After experiment | Control | After experiment | Staphylococcus aureus | Coli |
| Comparative Example 1 | 0.6 | 4.3 | 1,500,000 | 410,000 | 22,000,000 | 1,000 | 72.7% | 99.9955% |
| Example | 5.1 | 7.0 | 3,500,000 | 28 | 26,000,000 | 3 | 99.9992% | 99.99999% |
| Comparative Example 2 | 3.0 | 5.1 | 260,000 | 260 | 28,000,000 | 220 | 99.9% | 99.9992% |

Comparative Example 1 is a substrate that did not undergo an antibacterial treatment, and Comparative Example 2 is a commercially available antibacterial copper film. As shown in Table 1, Example according to the present disclosure exhibited good antibacterial activity. In addition, a change in antibacterial activity was measured over time, and it was confirmed that there was only little change in the antibacterial activity.

In addition, the example of the present disclosure exhibited a pencil hardness of 7H. With this hardness, when the antibacterial layer is applied to a touch panel or an operation button of an electronic device, the surface of the touch panel or the operation button can be physically protected due to the increased hardness can exhibit a good antibacterial activity. In addition, it can well fit a cover window of a flexible display because it has good folding characteristics.

As described above, the objective of the present disclosure is to provide a cover window with antibacterial patterns regularly and uniformly distributed over the entire area thereof. Thus, the cover window has a long-lasting and excellent antibacterial property over the entire area thereof.

In addition, due to the formation of embossed antibacterial patterns and inlay antibacterial patterns, the antibacterial property is improved and the bonding strength between the substrate and the antibacterial material is increased. For this reason, the manufactured cover window exhibits improved abrasion resistance and a long-lasting antibacterial property.

What is claimed is:

1. An antibacterial cover window comprising:
    a substrate; and
    an antibacterial pattern formed on the substrate,
    wherein the antibacterial pattern is an embossed pattern protruding from an upper surface of the substrate or an inlay pattern embedded in an intaglio pattern etched into the substrate,
    wherein the antibacterial pattern has a horizontal width in the range from 50 to 5000 nm, an average spacing in the range from 50 to 5000 nm, and an average height in the range from 0.5 to 500 nm, and
    wherein a surface of the antibacterial pattern is roughened.

2. The antibacterial cover window of claim 1, wherein the surface of the antibacterial pattern is roughened through a surface shape control process.

3. The method of claim 1, wherein the antibacterial pattern is made of one material or a mixture of two or more materials selected from among silver, platinum, copper, and carbon dioxide.

4. The antibacterial cover window of claim 1, wherein the antibacterial pattern has a pencil hardness in the range from 3H to 9H.

5. The antibacterial cover window of claim 1, wherein the substrate is a glass plate or a polymer film.

* * * * *